United States Patent
Aikoh

(10) Patent No.: US 8,888,291 B2
(45) Date of Patent: Nov. 18, 2014

(54) POLARIZATION OPTICAL APPARATUS HAVING SLIDABLE POLARIZATION ELEMENT

(75) Inventor: Yoshihisa Aikoh, Kanagawa (JP)

(73) Assignee: Sony Corporation, Tokyo (JP)

( * ) Notice: Subject to any disclaimer, the term of this patent is extended or adjusted under 35 U.S.C. 154(b) by 196 days.

(21) Appl. No.: 13/593,960

(22) Filed: Aug. 24, 2012

(65) Prior Publication Data

US 2013/0057831 A1    Mar. 7, 2013

(30) Foreign Application Priority Data

Sep. 2, 2011    (JP) ................................ 2011-191191

(51) Int. Cl.
| | | |
|---|---|---|
| *G03B 21/20* | (2006.01) | |
| *G02B 27/28* | (2006.01) | |
| *H04N 9/31* | (2006.01) | |
| *G02F 1/1335* | (2006.01) | |
| *G02B 27/26* | (2006.01) | |

(52) U.S. Cl.
CPC .......... *G02B 21/2073* (2013.01); *H04N 9/3167* (2013.01); *G02F 1/133528* (2013.01); *G02B 27/26* (2013.01); *G02B 27/286* (2013.01)
USPC .................. 353/20; 353/31; 353/34; 353/37; 359/490.01; 359/490.03; 349/8; 349/58

(58) Field of Classification Search
CPC ...... G03B 21/2073; G03B 21/20; H04N 9/31; H04N 9/3105; H04N 9/3108; H04N 9/3167; H04N 9/3197; G02B 5/30; G02B 5/3025; G02B 5/3083; G02B 27/28; G02B 27/286; G02F 1/133528; G02F 1/133533; G02F 1/133536
USPC .............. 353/20, 30–31, 33–34, 37; 349/1, 5, 349/7–9, 58, 60; 359/489.02, 489.2, 359/490.01–490.03
See application file for complete search history.

(56) References Cited

U.S. PATENT DOCUMENTS

| | | | | |
|---|---|---|---|---|
| 6,611,381 | B2 * | 8/2003 | Kodama et al. | 359/619 |
| 6,642,977 | B2 * | 11/2003 | Kotchick et al. | 349/96 |
| 6,851,810 | B2 * | 2/2005 | Arai et al. | 353/15 |
| 6,854,848 | B2 * | 2/2005 | Fujimori et al. | 353/20 |
| 8,186,832 | B2 * | 5/2012 | Hayashi et al. | 353/20 |
| 8,641,206 | B2 * | 2/2014 | Nakano et al. | 353/97 |
| 2005/0117122 | A9 * | 6/2005 | Ito et al. | 353/57 |
| 2005/0185141 | A1 * | 8/2005 | Fujita et al. | 353/20 |
| 2006/0176561 | A1 * | 8/2006 | Kitabayashi | 359/569 |
| 2006/0215130 | A1 * | 9/2006 | Nakamura et al. | 353/97 |

(Continued)

FOREIGN PATENT DOCUMENTS

| | | |
|---|---|---|
| JP | 2008-158225 | 7/2008 |
| JP | 2008-180856 | 8/2008 |
| JP | 2008-197185 | 8/2008 |

*Primary Examiner* — Georgia Y Epps
*Assistant Examiner* — Jori S Reilly-Diakun
(74) *Attorney, Agent, or Firm* — Frommer Lawrence & Haug LLP; William S. Frommer

(57) ABSTRACT

A polarization optical apparatus including a reflection-type polarization element for transmitting a predetermined polarization component light. A slidably supported reflection-type optical modulation element is held by a holding member that includes a sliding support surface for slidably supporting the reflection-type polarization element. The reflection-type polarization element is urged toward the sliding support surface while the reflection-type polarization element is enabled to be slid along the sliding support surface.

14 Claims, 13 Drawing Sheets

(56) References Cited

U.S. PATENT DOCUMENTS

| | | | |
|---|---|---|---|
| 2008/0055546 A1* | 3/2008 | DeCusatis et al. | 353/7 |
| 2008/0111973 A1* | 5/2008 | Aruga | 353/20 |
| 2008/0198334 A1* | 8/2008 | Kasazumi et al. | 353/38 |
| 2010/0201952 A1* | 8/2010 | Sakai | 353/20 |

* cited by examiner

300 POLARIZATION OPTICAL APPARATUS

POLARIZATION OPTICAL APPARATUS HAVING SLIDABLE POLARIZATION ELEMENT

BACKGROUND

The present technology relates to a polarization optical apparatus, an optical apparatus, and a projection apparatus.

In a projector (a projection apparatus) that is one image display device, a discharge lamp is widely used as a light source and a transmission-type liquid crystal element or a DMD (Digital Micromirror Device) is widely used as an image modulation element. Also, a device and an optical component have been enhanced. Further, in recent years, a projection-type image display device using a higher resolution reflection-type liquid crystal panel (a reflection-type optical modulation element) has also been put into practical use.

Improved brightness and contrast of an image to be displayed are important elements in gaining an advantage in the projector market. When a light amount of a light source increases to brighten an image to be displayed by a projector, temperatures of parts on an optical path rise. The rise in temperature of the parts on the optical path causes an error in an optical positional relationship due to a difference in linear expansion coefficient between constituent parts and causes degradation of image quality of a projected image such as a change in focus position of the projected image or a change in projection position.

Because of this, as a heat solution for a projector, for example, a holder having a small linear expansion coefficient such as glass is used to fix the polarization plate, and a gap between the holder and the polarization plate is sealed, for example, using a silicon rubber-based adhesive for dust proofing.

Further, a projection-type display device in which a polarization plate (a wire grid polarizer) is fixed using a fixing spring member instead of a fixing method using an adhesive has been proposed.

RELATED ART LITERATURE

Patent Literature

[Patent Literature 1] Japanese Patent Application Laid-Open No. 2008-180856

SUMMARY

However, in a reflection-type liquid crystal panel, even when a difference in a linear expansion coefficient between a holder and a polarization plate is small due to a smaller pixel pitch, adhesion and fixation over an entire circumference of the polarization plate causes thermal distortion due to a difference in a linear expansion coefficient between different types of materials. Because of this, the polarization plate is deformed with a curvature on a reflection surface of a ray, and an error is generated in a focus on a projection surface or registration deviation is generated in respective R, G and B projected images.

Further, even when the polarization plate is fixed using a fixing spring member, there is a difference in a fixing position and a fixing method. However, since a linear expansion coefficient still differs and the polarization plate is fixed at three points, the polarization plate is distorted.

The present technology has been made in view of the circumstances described above, and an object of the present disclosure is to provide a polarization optical apparatus, an optical apparatus, and a projection apparatus capable of reducing influence of heat deformation and improving precision of image performance.

In order to resolve the above object, a polarization optical apparatus includes a reflection-type polarization element, a polarization element holding member, and an urging portion. The reflection-type polarization element transmits a predetermined polarization component light, inputs the light to a reflection-type optical modulation element, and reflects polarization component light optically modulated by the reflection-type optical modulation element. The polarization element holding member includes a sliding support surface for slidably supporting the reflection-type polarization element in a surface direction, and holds the reflection-type polarization element. The urging portion urges the reflection-type polarization element toward the sliding support surface while enabling the reflection-type polarization element to be slid along the sliding support surface.

Further, in order to resolve the above object, an optical apparatus includes a plurality of polarization optical apparatuses and a color synthesis prism. The plurality of polarization optical apparatuses output polarization component lights optically modulated by reflection-type optical modulation elements. The color synthesis prism receives, synthesizes and outputs the polarization component lights from the plurality of the polarization optical apparatuses.

Further, the polarization optical apparatus includes a reflection-type polarization element, a polarization element holding member, and an urging portion. The reflection-type polarization element transmits a predetermined polarization component light, inputs the light to a reflection-type optical modulation element, and reflects polarization component light optically modulated by the reflection-type optical modulation element. The polarization element holding member includes a sliding support surface for slidably supporting the reflection-type polarization element in a surface direction, and holds the reflection-type polarization element. The urging portion urges the reflection-type polarization element toward the sliding support surface while enabling the reflection-type polarization element to be slid along the sliding support surface.

Further, in order to resolve the above object, a projection apparatus includes a light source, a separation optical component, reflection-type optical modulation elements, an optical apparatus and a projection unit. The separation optical component separates an output light from the light source according to wavelength bands. The plurality of reflection-type optical modulation elements optically modulate and reflect the incident light separated according to wavelength bands. The optical apparatus synthesizes and outputs lights according to the wavelength bands after the optical modulation in the reflection-type optical modulation elements. The projection unit projects and outputs an output light from the optical apparatus.

Further, the optical apparatus includes a plurality of polarization optical apparatuses, and a color synthesis prism. The plurality of polarization optical apparatuses output polarization component lights optically modulated by the reflection-type optical modulation elements. The color synthesis prism receives, synthesizes and outputs the polarization component lights from the plurality of the polarization optical apparatuses.

Further, the polarization optical apparatus includes a reflection-type polarization element, a polarization element holding member and an urging portion. The reflection-type polarization element transmits a predetermined polarization component light, inputs the light to the reflection-type optical modulation elements, and reflects the polarization component lights optically modulated by the reflection-type optical modulation elements. The polarization element holding member includes a sliding support surface for slidably supporting the reflection-type polarization element in a surface direction, and holds the reflection-type polarization element. The urging portion urges the reflection-type polarization element toward the sliding support surface while enabling the reflection-type polarization element to be slid along the sliding support surface.

According to the polarization optical apparatus, the optical apparatus, and the projection apparatus, it is possible to reduce influence of heat deformation and improve precision of image performance

DETAILED DESCRIPTION OF THE EMBODIMENTS

Figure 1:
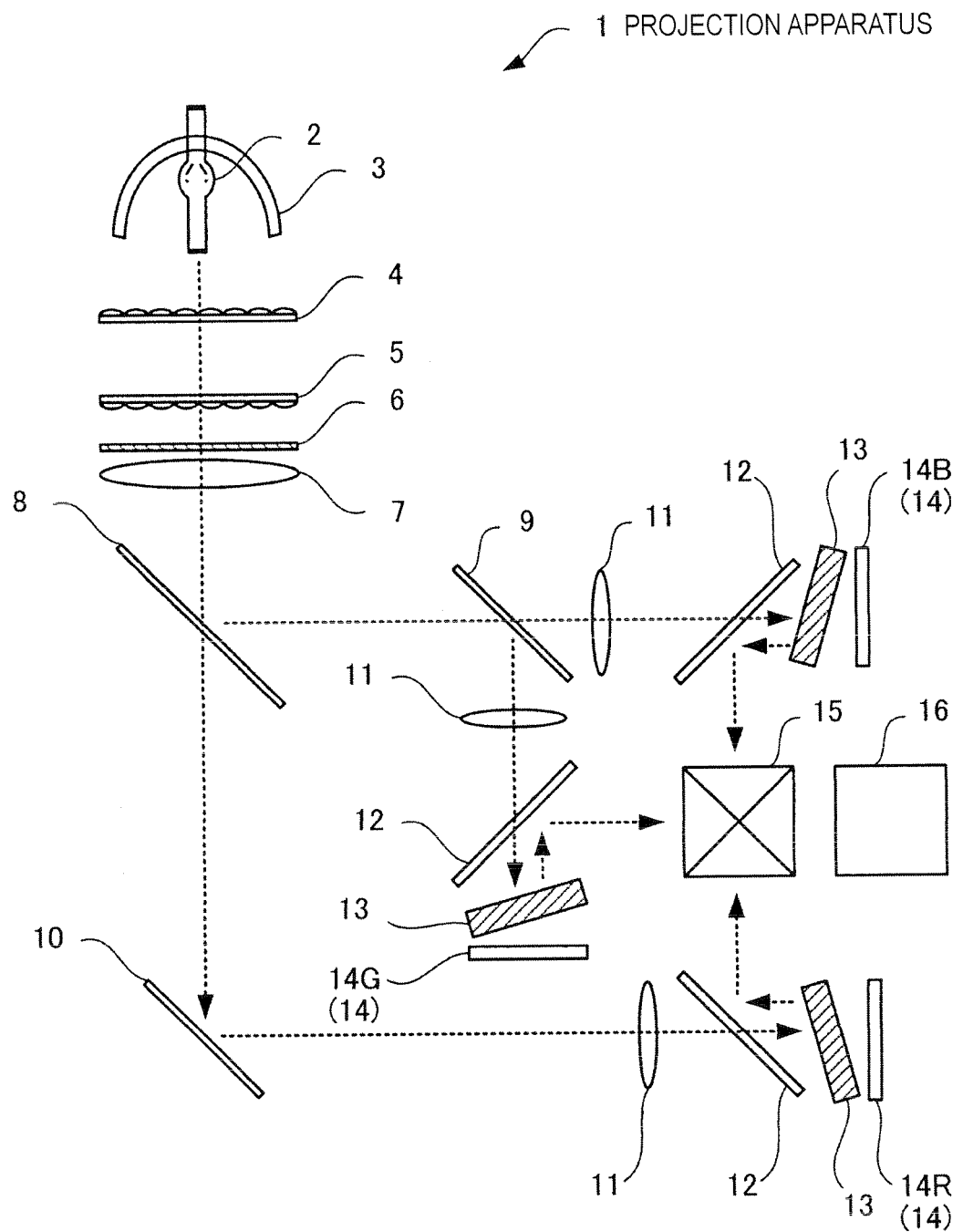
FIG. 1 is a diagram showing a configuration example of a projection apparatus of an embodiment.

Hereinafter, preferred embodiments of the present technology will be described in detail with reference to the appended drawings. Note that, in this specification and the appended drawings, structural elements that have substantially the same function and structure are denoted with the same reference numerals, and repeated explanation of these structural elements is omitted.

Hereinafter, embodiments of the present technology will be described with reference to the accompanying drawings. First, an overall configuration of a projection apparatus of an embodiment will be described with reference to FIG. 1. FIG. 1 is a diagram showing a configuration example of the projection apparatus of the embodiment.

The projection apparatus 1 includes a light source 2, a reflector 3, a fly-eye lens 4, a fly-eye lens 5, a polarization beam splitter (a polarization element) 6, a condenser lens 7, a separation and synthesis optical component, and a projection lens (a projection optical component) 16.

The light source 2 is, for example, an HID (High Intensity Discharge) lamp such as an ultra-high pressure mercury lamp or a metal halide lamp, and outputs white light. The light source 2 is arranged in a focus position of the reflector 3, and the reflector 3 reflects the white light output from the light source 2 to generate substantially parallel light.

The fly-eye lens (a first fly-eye lens) 4 and the fly-eye lens (a second fly-eye lens) 5 receive the substantially parallel light reflected by the reflector 3, and output to the polarization beam splitter 6. The fly-eye lens 4 and the fly-eye lens 5 uniformize illuminance of the light to be incident on reflection-type optical modulation elements 14 that will be described later.

The polarization beam splitter 6 aligns a polarization axis of the output light in a predetermined direction. For example, the polarization beam splitter 6 receives light including s-polarized light and p-polarized light and outputs the p-polarized light. The condenser lens 7 receives and condenses the output light of the polarization beam splitter 6. White light output from the condenser lens 7 is incident on the separation and synthesis optical component.

The separation and synthesis optical component separates incident light from the condenser lens 7 into R, G and B (red, green, and blue). The respective lights are spatially modulated by reflection-type optical modulation elements 14 and then synthesized. Output light forms a projected image. The separation and synthesis optical component includes a dichroic mirror 8, a dichroic mirror 9, a mirror (a reflection mirror) 10, field lenses 11, reflection-type polarization elements 12, optical compensation elements 13, the reflection-type optical modulation elements 14, and a color (light) synthesis prism 15. The reflection-type optical modulation elements 14 include a reflection-type optical modulation element 14R for spatially modulating light in a red wavelength band, a reflection-type optical modulation element 14G for spatially modulating light in a green wavelength band, and a reflection-type optical modulation element 14B for spatially modulating light in a blue wavelength band.

The dichroic mirror 8 and the dichroic mirror 9 selectively transmit or reflect the respective RGB lights using their wavelength bands. The dichroic mirror 8 transmits light in a red wavelength band and reflects lights in a green wavelength band and a blue wavelength band. The dichroic mirror 9 transmits the light in the blue wavelength band and reflects the light in the green wavelength band. Accordingly, the white light is separated into three primary colors of RGB. The mirror 10 reflects the light in the red wavelength band.

The color-separated light beams are incident on the field lenses 11 and the reflection-type polarization elements 12 and illuminate the reflection-type optical modulation element 14R, the reflection-type optical modulation element 14G, and the reflection-type optical modulation element 14B, respectively. The reflection-type polarization elements 12 may be, for example, polarization beam filters or wire grid polarization plates.

The respective RGB lights light-modulated by the reflection-type optical modulation element 14R, the reflection-type optical modulation element 14G, and the reflection-type optical modulation element 14B are optically compensated (fine adjustment of a phase modulation amount) by the optical compensation elements 13 and then incident on the reflection-type polarization elements 12. The optical compensation elements 13 are provided with a predetermined slope with respect to the reflection-type optical modulation elements 14 in a pair in order to obtain more suitable optical compensation. Again, each of the RGB lights incident on the reflection-type polarization element 12 is partially transmitted through the reflection-type polarization element 12 and returned toward the light source 2 and is partially reflected and incident on the color synthesis prism 15 according to a degree of optical modulation. Further, various materials such as sapphire, crystal and TAC (triacetyl cellulose) may be used as materials of the optical compensation elements 13.

The color synthesis prism 15 transmits the incident light in the green wavelength band and reflects the incident lights in the red wavelength band and the blue wavelength band toward the projection lens 16. The color synthesis prism 15 is formed, for example, by bonding a plurality of glass prisms (four right-angled isosceles prisms having substantially the same shape) (a prism block), and two of first and second interference filters having a predetermined optical characteristic are formed on a bonding surface of each glass prism. The first interference filter reflects the incident light in the blue wavelength band and transmits the incident lights in the red wavelength band and the green wavelength. The second interference filter reflects the incident light in the red wavelength band and transmits the incident lights in the green wavelength band and the blue wavelength band. Accordingly, the respective RGB lights modulated by the reflection-type optical modulation element 14R, the reflection-type optical modulation element 14G, and the reflection-type optical modulation element 14B are synthesized by the color synthesis prism 15 and incident on a projection lens 16.

The projection lens 16 expands the output light from the separation and synthesis optical component to a predetermined magnification and projects an image to a screen (not shown).

Figure 2:
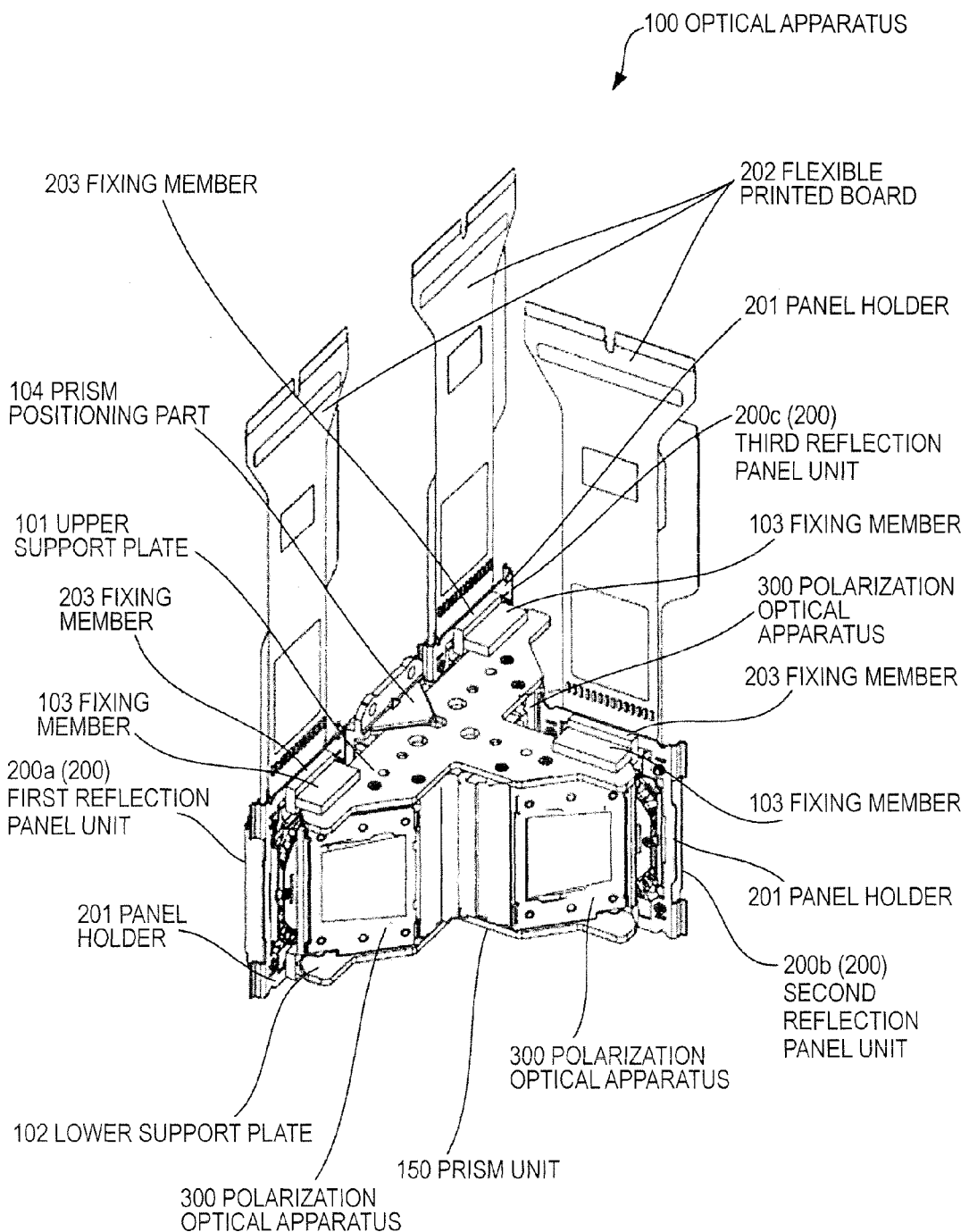
FIG. 2 is a perspective view of the optical apparatus of the embodiment.
Figure 3:
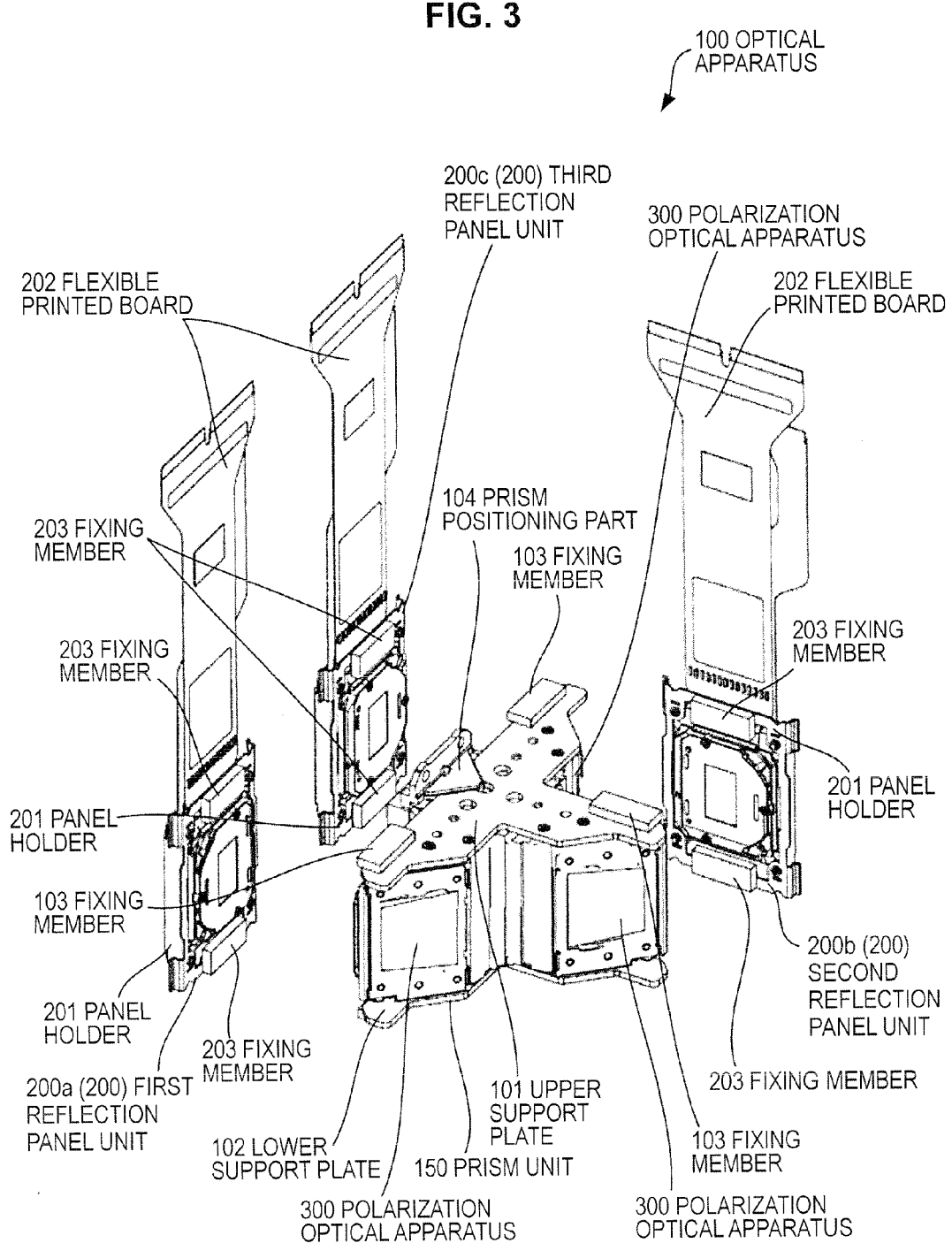
FIG. 3 is an exploded perspective view of the optical apparatus of the embodiment.

Next, an overview of an optical apparatus of an embodiment will be described with reference to FIGS. 2 and 3. FIG. 2 is a perspective view of the optical apparatus of the embodiment. FIG. 3 is an exploded perspective view of the optical apparatus of the embodiment.

An optical apparatus 100 constitutes the separation and synthesis optical component of the projection apparatus 1 together with the dichroic mirror 8, the dichroic mirror 9, the mirror (reflection mirror) 10, and the field lenses 11. The optical apparatus 100 spatially modulates the respective color-separated RGB (red, green, blue) lights using the reflection-type optical modulation elements 14 and then synthesizes the lights. A projected image is formed by an output light of the optical apparatus.

The optical apparatus 100 includes a prism unit 150, a first reflection panel unit (a first light modulation unit) 200a, a second reflection panel unit (a second light modulation unit) 200b, and a third reflection panel unit (a third light modulation unit) 200c.

The first reflection panel unit 200a includes a reflection-type optical modulation element 14B and modulates light in the blue wavelength band. The second reflection panel unit 200b includes a reflection-type optical modulation element 14G and modulates light in the green wavelength band. The third reflection panel unit 200c includes a reflection-type optical modulation element 14R and modulates light in the red wavelength band.

In the three reflection panel units 200 (the first reflection panel unit 200a, the second reflection panel unit 200b, and the third reflection panel unit 200c), the optical compensation element 13 and the reflection-type optical modulation element 14 are held in a panel holder. The reflection panel unit 200 includes fixing members 203 provided in an upper end portion and a lower edge portion of a panel holder 201 in a picture frame shape.

Figure 4:
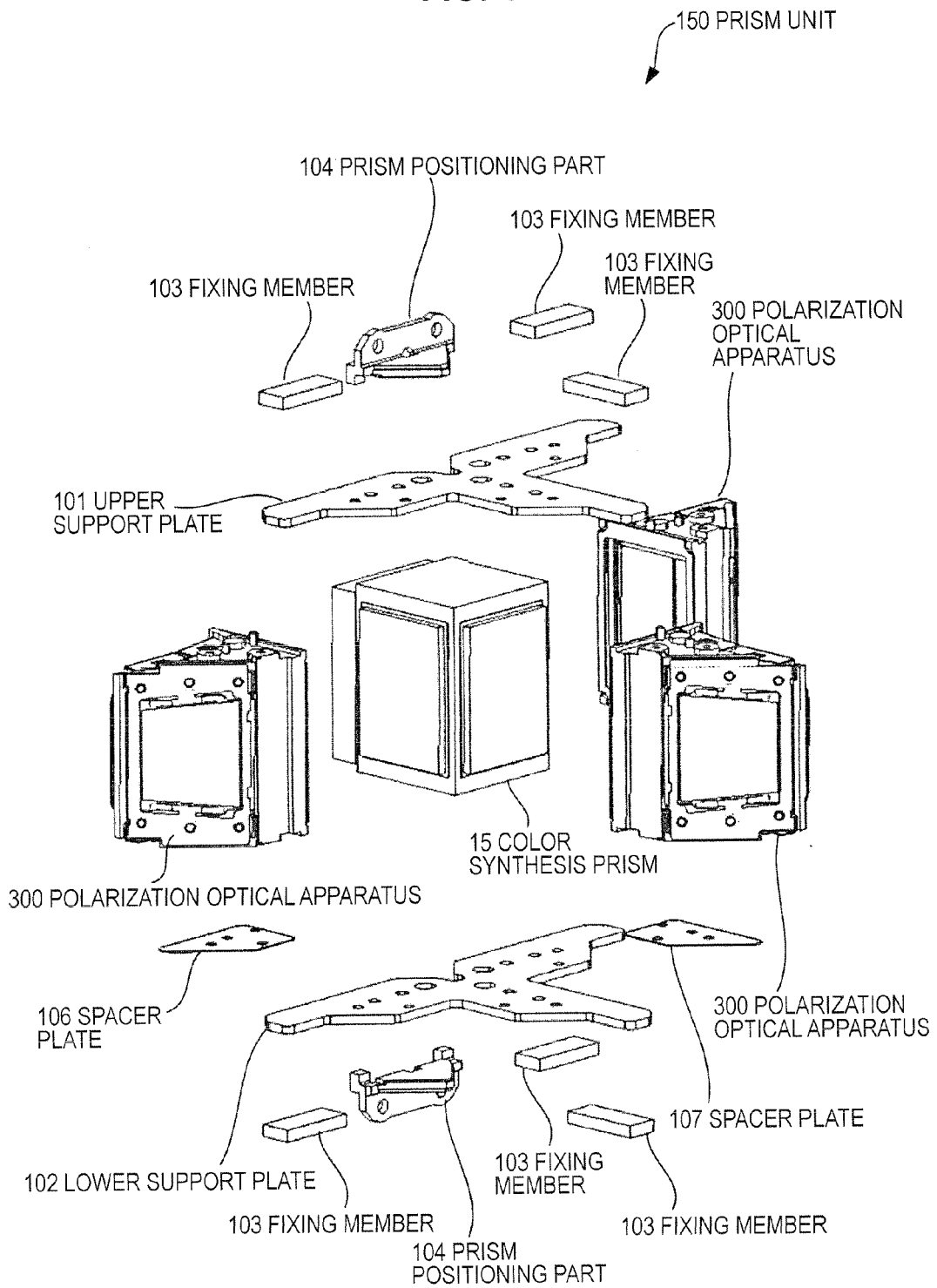
FIG. 4 is a partially exploded perspective view of a prism unit of an embodiment.

Next, an overview of the prism unit 150 of the embodiment will be described with reference to FIG. 4. FIG. 4 is a partially exploded perspective view of the prism unit of the embodiment.

The prism unit 150 includes a color synthesis prism 15, and three polarization optical apparatuses 300 arranged on three sides around the color synthesis prism 15. The color synthesis prism 15 and the three polarization optical apparatuses 300 are sandwiched and supported between the upper support plate 101 and the lower support plate 102.

In this case, one of the three polarization optical apparatuses 300 is supported in a different vertical direction from the two other polarization optical apparatuses 300. Because of this, the polarization optical apparatus 300 in the different vertical direction is supported between the upper support plate 101 and the lower support plate 102 via a spacer plate 106. Further, the two other polarization optical apparatuses 300 are supported between the upper support plate 101 and the lower support plate 102 via a spacer plate 107 (the other one is not shown).

Each of the upper support plate 101 and the lower support plate 102 includes fixing members 103 provided in respective mounting positions of the three reflection panel units 200. The fixing members 103 are adhered and fixed to the corresponding fixing members 203 after mounting positions of the three reflection panel units 200 are adjusted with respect to the prism unit 150. Further, each of the upper support plate 101 and the lower support plate 102 includes a prism positioning part 104 that determines a positional relationship between the projection lens 16 and the prism unit 150.

Figure 5:
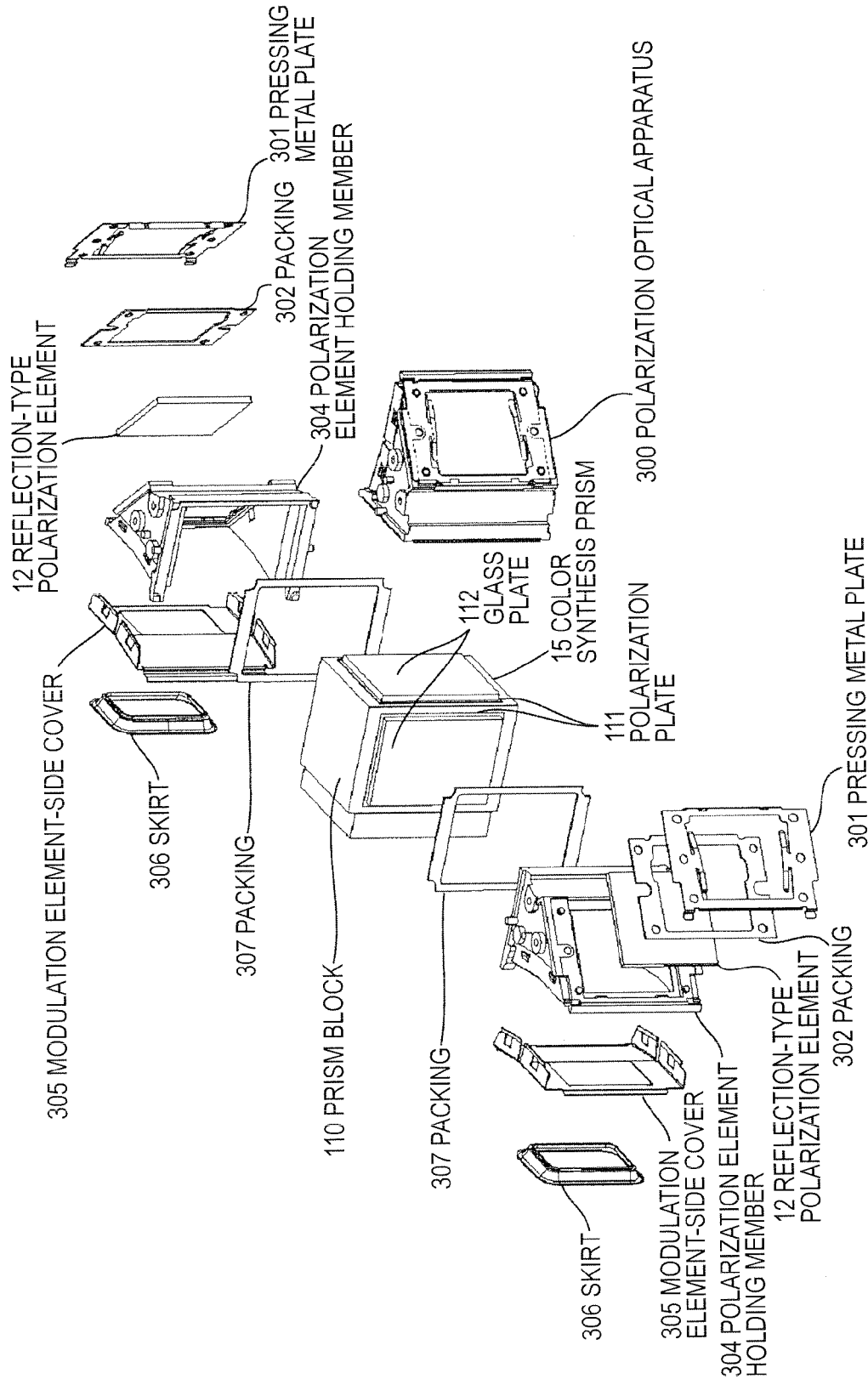
FIG. 5 is an exploded perspective view of a color synthesis prism and a polarization optical apparatus of an embodiment.

Next, an overview of the color synthesis prism 15 of the embodiment and three polarization optical apparatuses 300 arranged on three sides around the color synthesis prism 15 will be described with reference to FIG. 5. FIG. 5 is an exploded perspective view of the color synthesis prism and the polarization optical apparatus of the embodiment.

The color synthesis prism 15 includes polarization plates 111 and glass plates (incident glasses) 112 provided on the respective three side surfaces of the prism block 110 on which the polarization optical apparatuses 300 are arranged. The polarization plate 111 is included to be sandwiched between the prism block 110 and the glass plate 112. Each of the polarization plate 111 and the glass plate 112 is rectangular, similar to the side surface of the prism block 110. Sizes thereof are in a relationship of the side surface of the prism block 110>the polarization plate 111>the glass plate 112. The glass plate 112 is smaller than the inner peripheral portion that forms the window portion 360 of the packing 307 and does not interfere with the packing 307. The polarization optical apparatus 300 and the color synthesis prism 15 are assembled so that the packing 307 is sandwiched therebetween.

The polarization optical apparatus 300 is a columnar body having a substantially triangular prism shape, which has side surfaces: a surface (a first surface) including a reflection-type polarization element 12 and receiving light from the light source 2, a surface (a second surface) that the reflection-type optical modulation element faces, and a surface (a third surface) for outputting an optically modulated light to the color synthesis prism 15.

Figure 6:
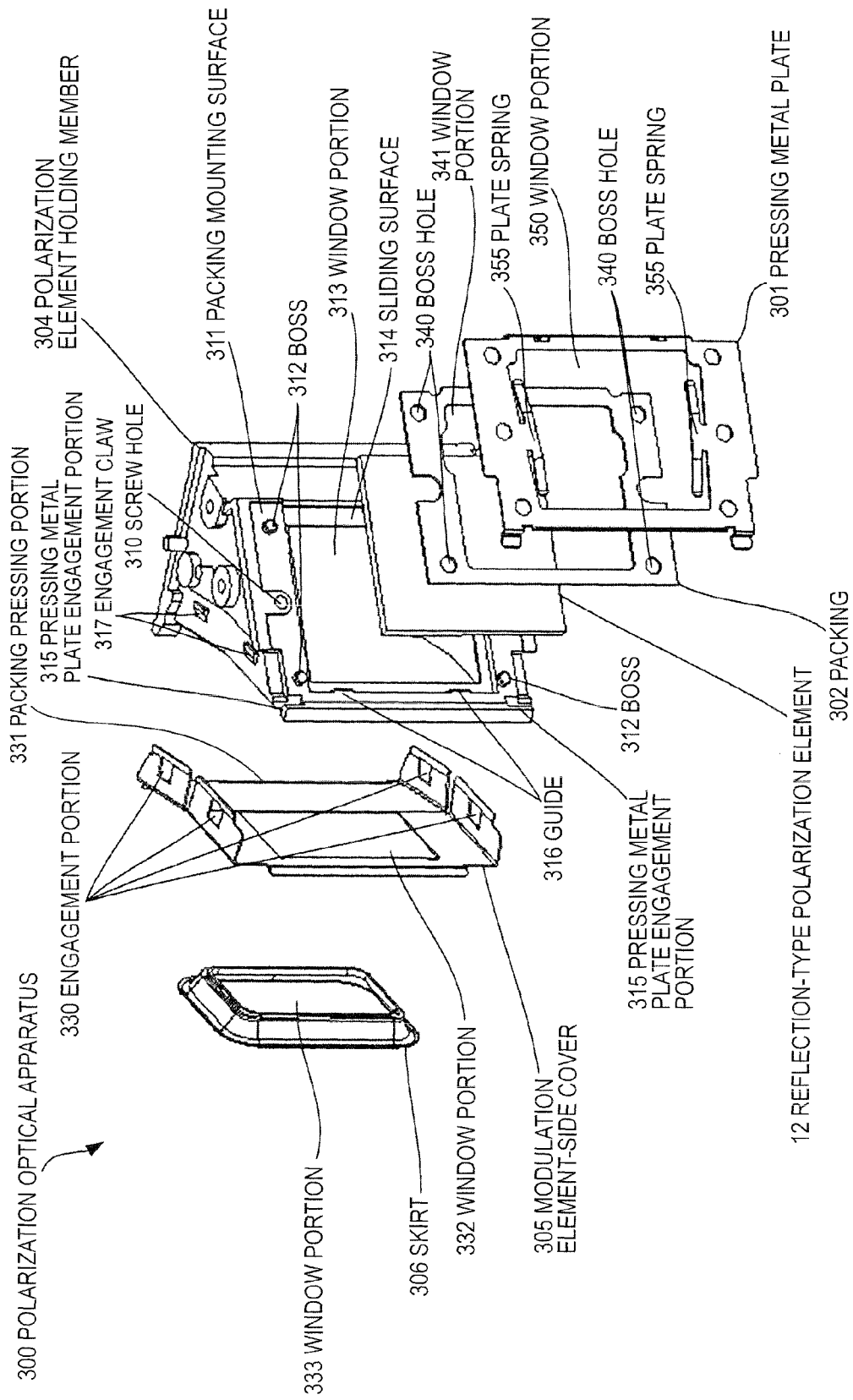
FIG. 6 is an exploded perspective view of a polarization optical apparatus of an embodiment.
Figure 7:
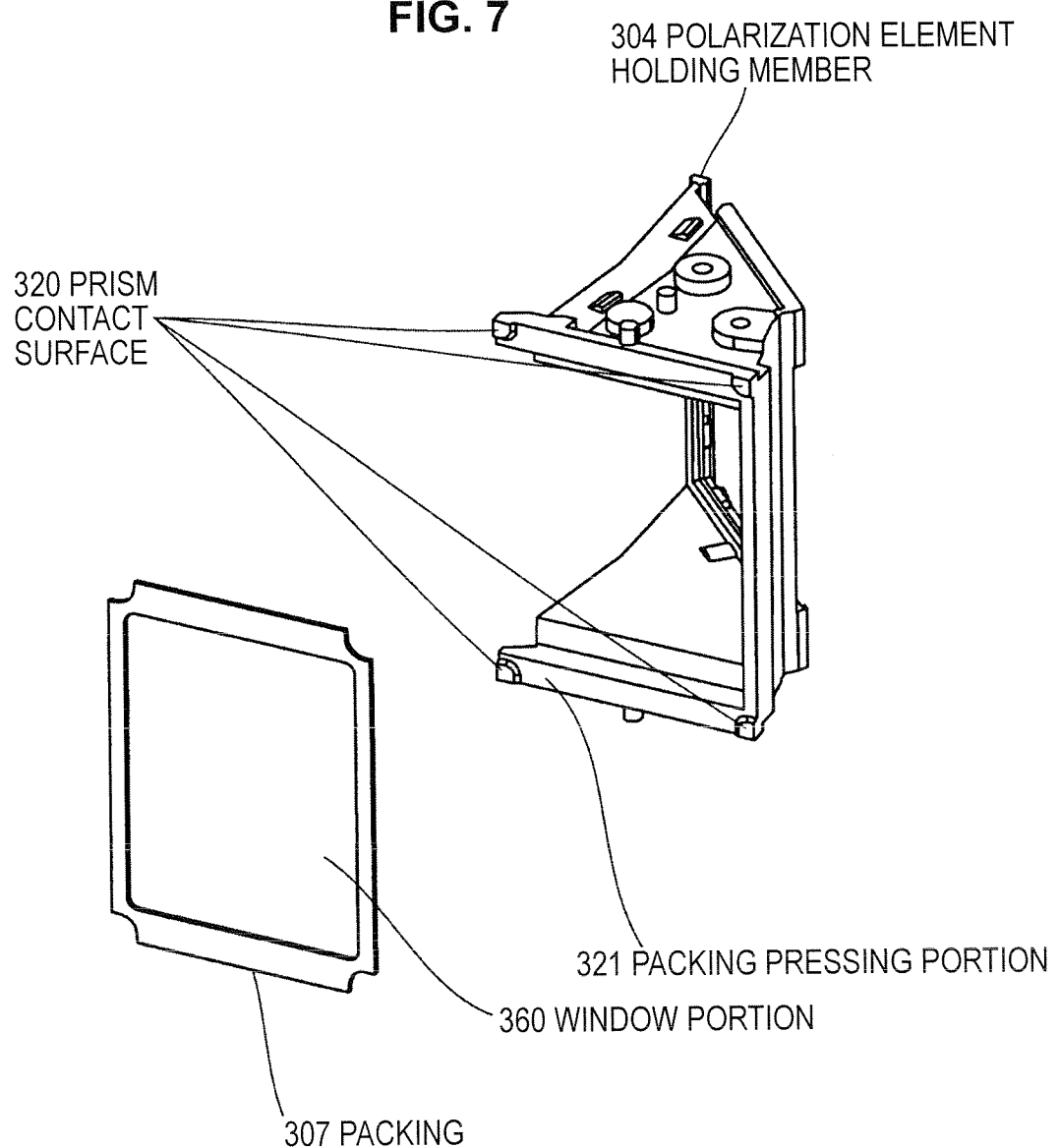
FIG. 7 is a view showing an overview of a polarization element holding member and a packing of an embodiment.
Figure 8:
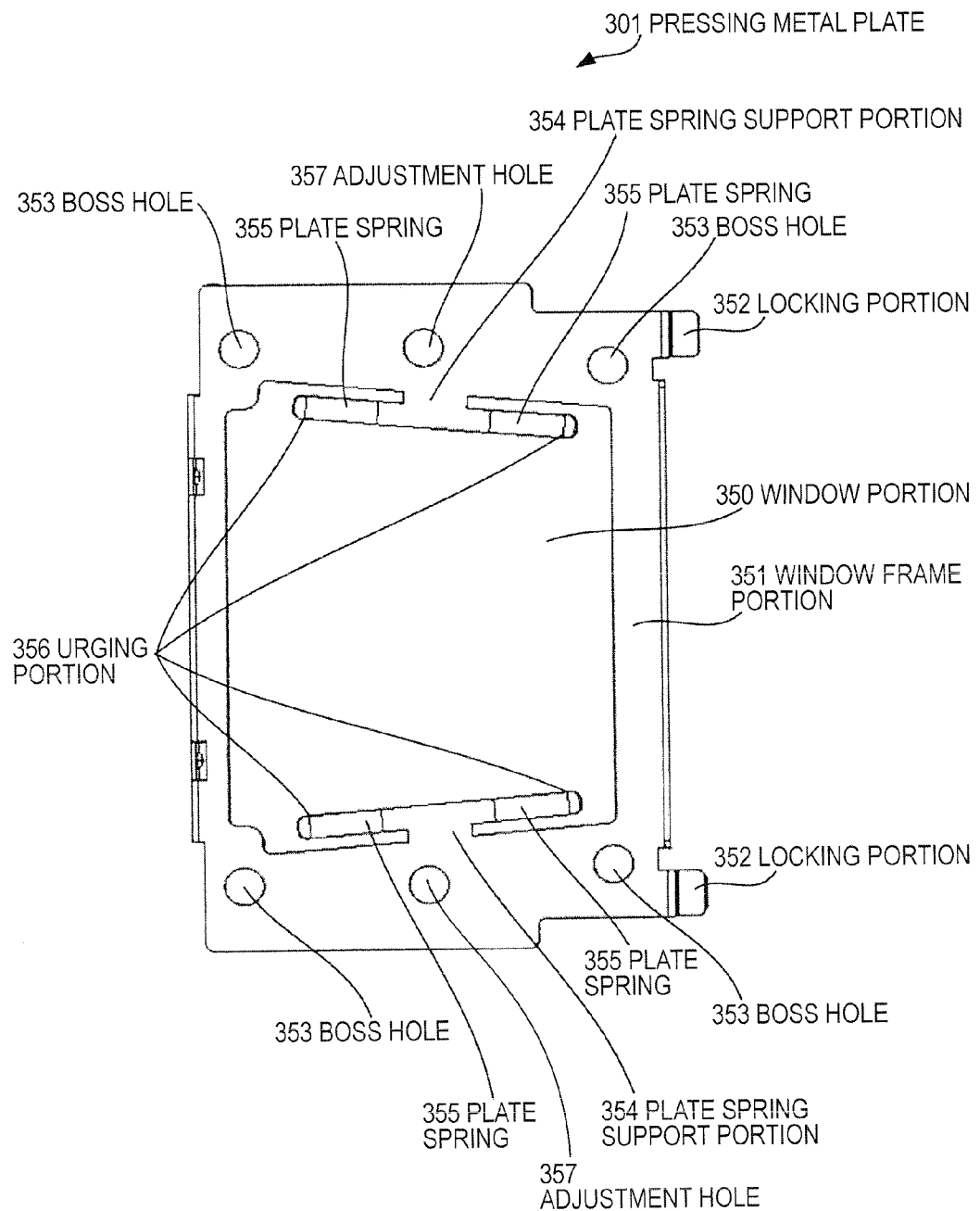
FIG. 8 is a view showing an overview of a pressing metal plate of an embodiment.
Figure 9:
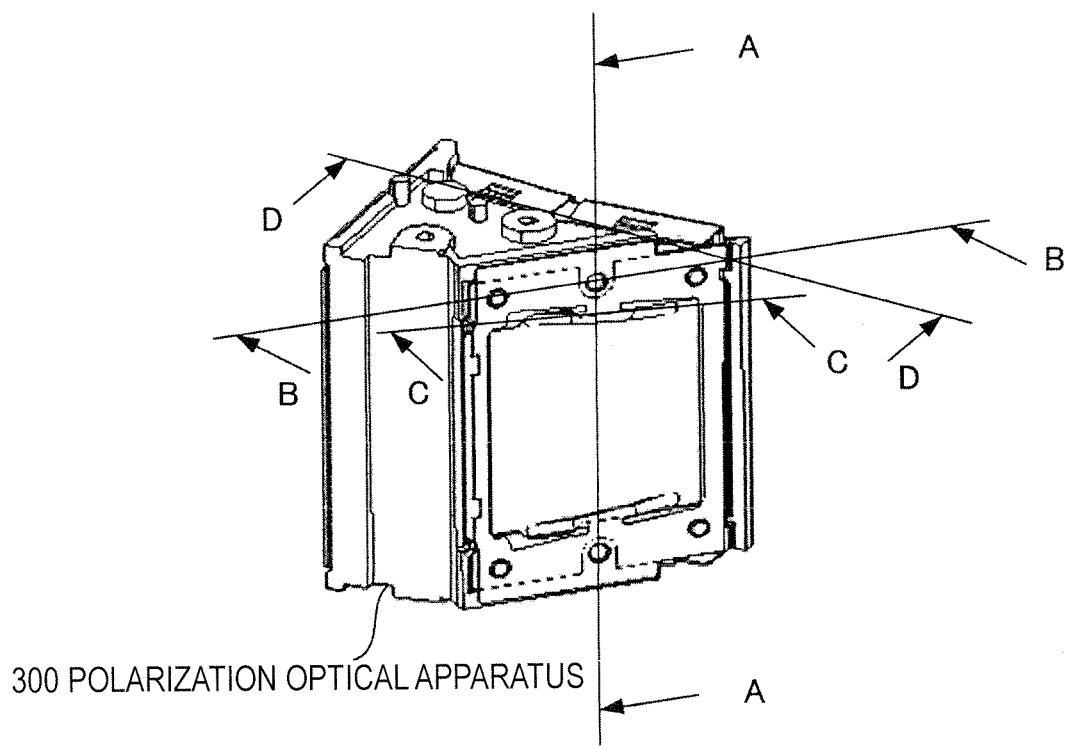
FIG. 9 is a perspective view of a polarization optical apparatus of an embodiment.
Figure 10:
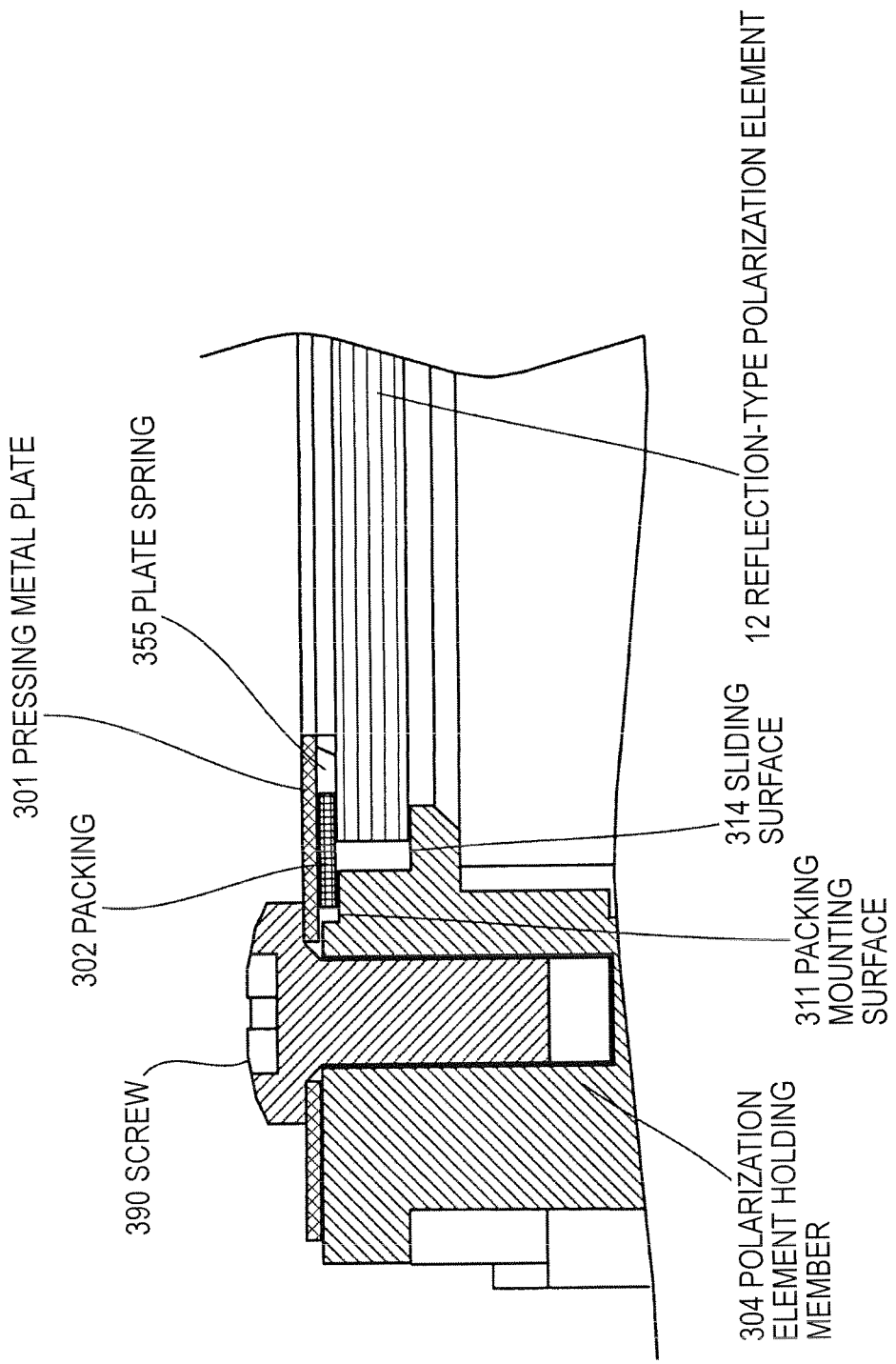
FIG. 10 is a cross-sectional view of a polarization optical apparatus of an embodiment taken along line A-A.
Figure 11:
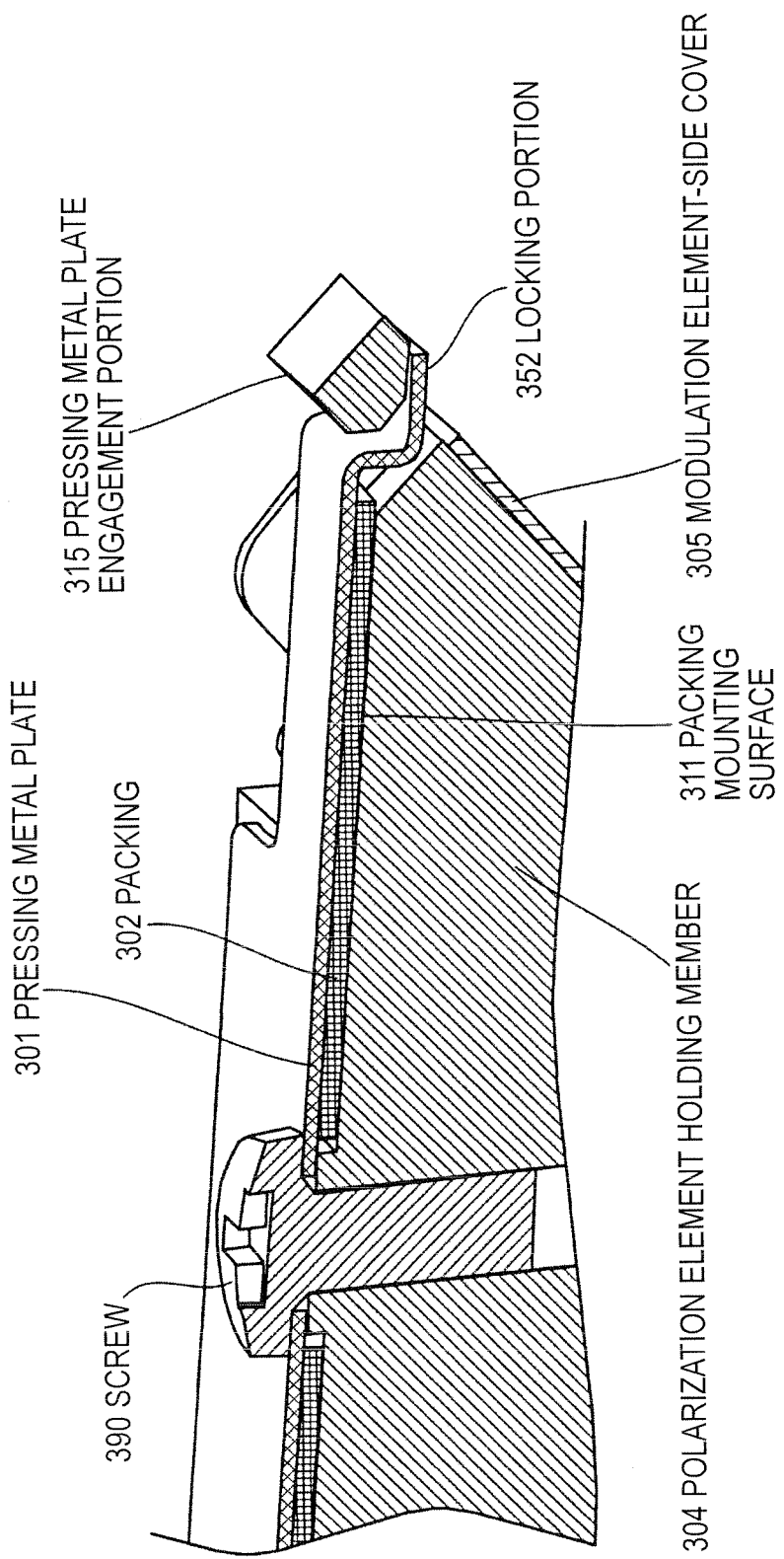
FIG. 11 is a cross-sectional view of the polarization optical apparatus of the embodiment taken along line B-B.
Figure 12:
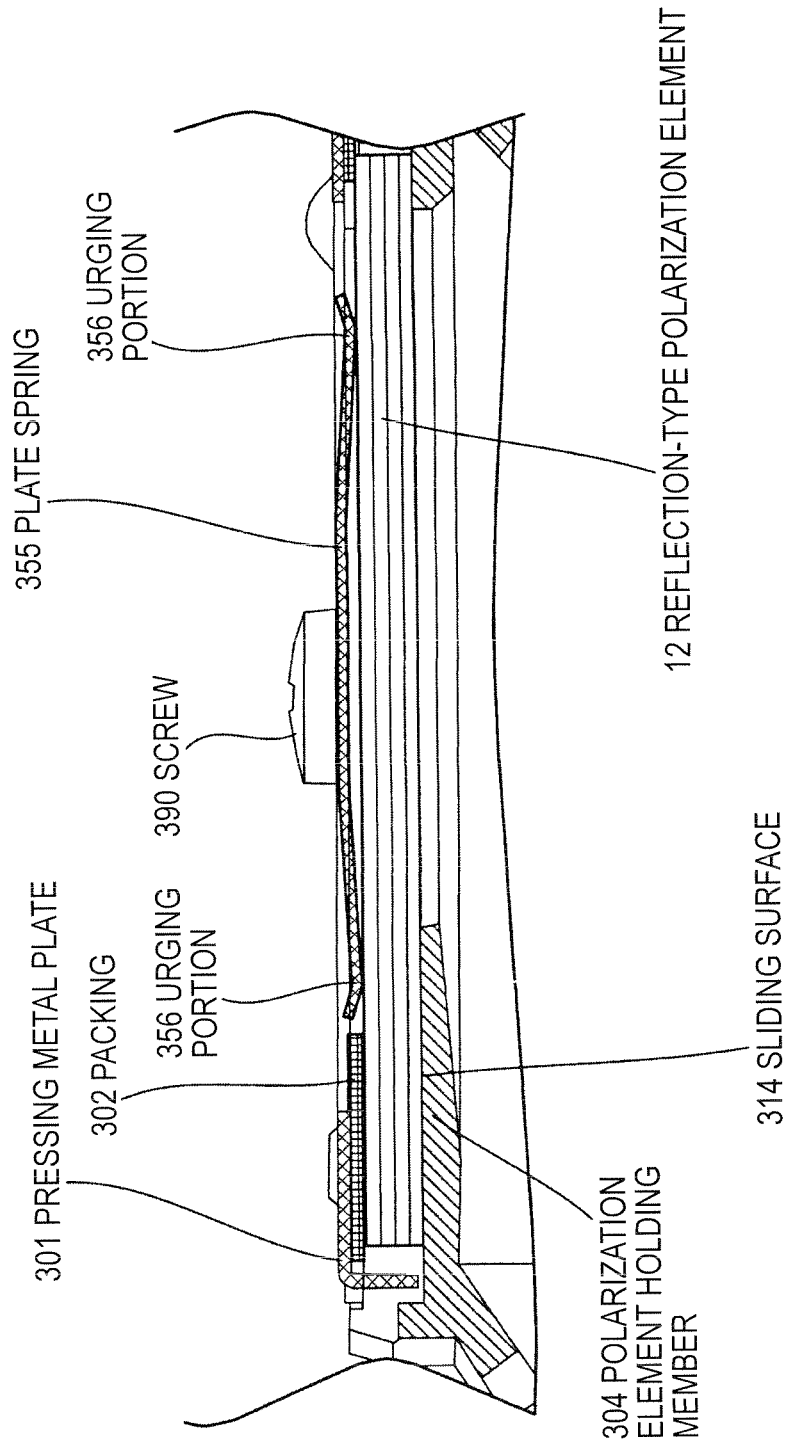
FIG. 12 is a cross-sectional view of the polarization optical apparatus of the embodiment taken along line C-C.
Figure 13:
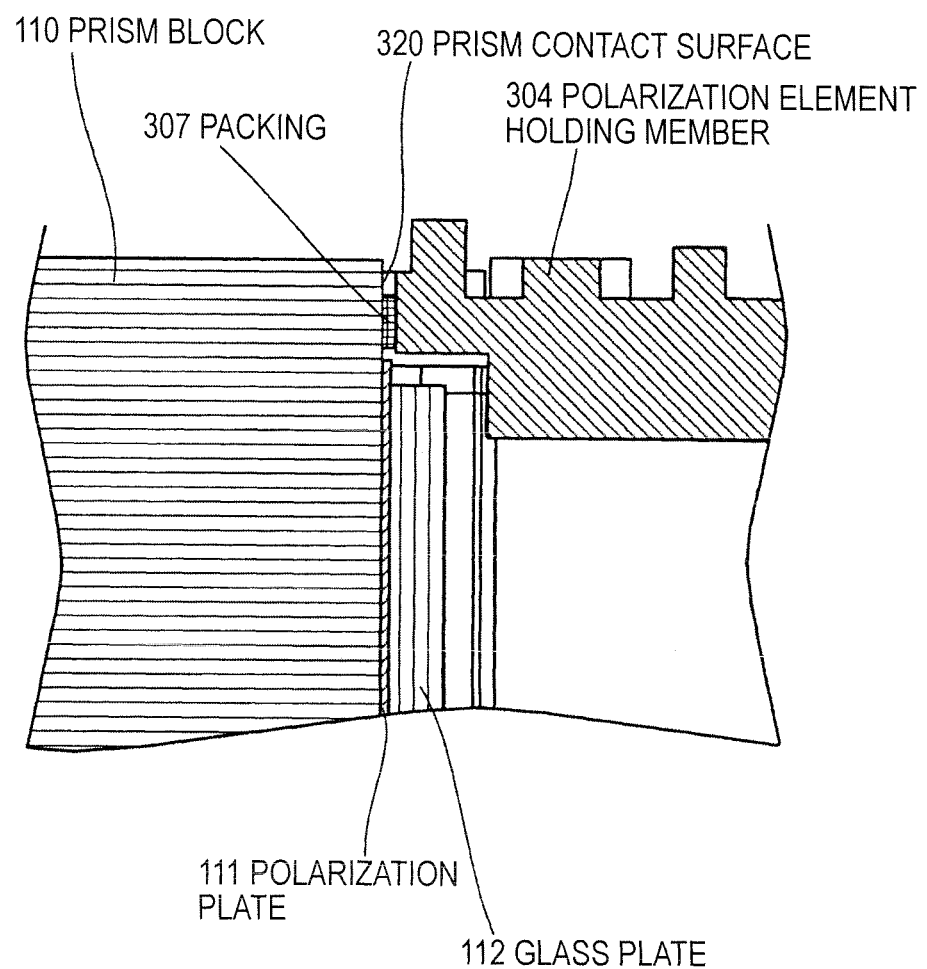
FIG. 13 is a cross-sectional view taken along line D-D when the polarization optical apparatus of the embodiment contacts a prism block.

Next, a configuration of the polarization optical apparatus 300 of the embodiment, and a structure in which the refection-type polarization element 12, the packing 302, and the pressing metal plate 301 are mounted on the polarization element holding member 304 will be described with reference to FIGS. 6 to 13. FIG. 6 is an exploded perspective view of a polarization optical apparatus of an embodiment. FIG. 7 is a view showing an overview of the polarization element holding member and the packing of the embodiment. FIG. 8 is a view showing an overview of the pressing metal plate of the embodiment. FIG. 9 is a perspective view of a polarization optical apparatus of an embodiment. FIG. 10 is a cross-sectional view of a polarization optical apparatus of an embodiment taken along line A-A. FIG. 11 is a cross-sectional view of the polarization optical apparatus of the embodiment taken along line B-B. FIG. 12 is a cross-sectional view of the polarization optical apparatus of the embodiment taken along line C-C. FIG. 13 is a cross-sectional view taken along line D-D when the polarization optical apparatus of the embodiment contacts the prism block.

The polarization optical apparatus 300 includes a pressing metal plate 301, a packing 302, a reflection-type polarization element 12, a polarization element holding member 304, a modulation element-side cover 305, and a skirt (packing) 306.

The polarization element holding member 304 is an aluminum housing having an upper surface and a lower surface in a trapezoidal (substantially triangular) shape. The polarization element holding member 304 is formed of aluminum having good thermal conductivity, and increases heat dissipation from the polarization element holding member 304 and uniformizes temperature distribution in a volume of the polarization optical apparatus 300.

The polarization element holding member 304 includes, in an upper surface and a lower surface, necessary bosses or screw holes for support by the upper support plate 101 and the lower support plate 102. Further, the polarization element holding member 304 includes necessary bosses for interposition of the spacer plates 106 and 107 between the polarization element holding member 304 and the lower support plate 102.

The polarization element holding member 304 includes a packing mounting surface 311 arranged in a picture frame shape on one side surface, and a window portion 313 on which the light from the light source 2 is incident is formed in the packing mounting surface 311. In the polarization element holding member 304, a frames faces, in an angular U-shape, two other surfaces (a surface that a reflection-type optical modulation element faces and a surface for outputting the optically modulated light to the color synthesis prism 15) without a pillar that separates a boundary of the two surfaces.

In the polarization element holding member 304, the packing mounting surface 311 and a sliding surface 314 are arranged in a step shape on the surface on which the light from the light source 2 is incident. Both the packing mounting surface 311 and the sliding surface 314 have a picture frame shape. The sliding surface 314 is smaller than the packing mounting surface 311 and arranged in a position deeper than the packing mounting surface 311. The polarization element holding member 304 includes pressing metal plate engagement portions 315 engaging with the pressing metal plate 301 and provided in an upper end and a lower end at one side of the surface on which the light from the light source 2 is incident.

The sliding surface 314 contacts a rim portion of the rectangle reflection-type polarization element 12 and slidably supports the reflection-type polarization element 12. The guides 316 are in a protrusion shape facing the sliding surface 314. A plurality of (e.g., two on a left side and two on a right side) guides are provided in a horizontal direction. The guides 316 guide sliding so that a slope of the polarization axis of the reflection-type polarization element 12 is not displaced. Further, the sliding surface 314 may be subjected to surface treatment for increasing a sliding property (e.g., mirror finishing or lubricant coating).

The packing 302 is mounted on the packing mounting surface 311. The packing mounting surface 311 includes bosses 312 provided at a total of four places, including two places of an upper portion and two places of a lower portion, and screw holes 310 provided at a total of two places, including one place in the vicinity of a center of the upper portion and one place in the vicinity of a center of the lower portion.

The packing 302 is formed of an elastic material (e.g., rubber) and seals a rim portion of the reflection-type polarization element 12. The packing 302 is in a schematically rectangular picture-frame shape, and includes boss holes 340 provided at four corners, and notches that flee the screw holes 310 at outer peripheral sides of two upper and lower places. The packing 302 includes a window portion 341 smaller than an external form of the reflection-type polarization element 12, and notches provided at two upper and lower places at an inner peripheral side that forms the window portion 341 in order to avoid interference with the plate springs 355.

The pressing metal plate 301 is formed of a metal such as aluminum and has a thin plate shape. The pressing metal plate 301 is schematically rectangular. The pressing metal plate 301 presses the packing 302, and includes plate springs 355 to urge the reflection-type polarization element 12 toward the sliding surface 314.

The pressing metal plate 301 includes locking portions 352 provided at an upper end and a lower end of one side. The pressing metal plate 301 includes boss holes 353 provided at four corners of a window frame portion 351 in a picture frame shape, and adjustment holes 357 provided substantially at centers of top and bottom sides. The window portion 350 has a substantially trapezoidal shape in which a side at which the locking portions 352 are provided is an upper base.

The plate springs 355 are supported by plate spring support portions 354 from the vicinity of the adjustment holes 357 of the window frame portion 351 and face the window portion 350. The plate springs 355 are bent from the plate spring support portions 354 toward the reflection-type polarization element 12, and include urging portions 356 bent in an opposite direction of the reflection-type polarization element 12 in the vicinity of tips.

The urging portions 356 are brought into contact with the reflection-type polarization element 12, in a linear shape having a bent plate width, and urge the reflection-type polarization element 12 toward the sliding surface 314. An urging force of the urging portions 356 is not intended to fix the reflection-type polarization element 12 to the sliding surface 314, but allows the reflection-type polarization element 12 to be slid along the sliding surface 314.

The urging force of the urging portions 356 can be adjusted by a tightening amount of screws 390 inserted into the adjustment holes 357. Since the adjustment holes 357 are included in the vicinity of the plate spring support portions 354 that support the plate springs 355, the urging force of the urging portions 356 is easily adjusted in response to the tightening amount of the screws 390.

The urging portions 356 are subjected to surface treatment (e.g., nickel plating) so that a sliding property with the reflection-type polarization element 12 can be improved. Further, while the example in which the urging portions 356 contact the reflection-type polarization element 12 in a linear shape has been shown, the urging portions 356 may contact the reflection-type polarization element 12 in a point shape. Further, the pressing metal plate 301 is not limited to the use of the plate springs 355 and may urge the reflection-type polarization element 12 using other urging means (e.g., elastic bodies such as rubber or coil springs).

In the polarization element holding member 304, the reflection-type polarization element 12 is mounted on the sliding surface 314, the packing 302 is mounted on the packing mounting surface 311, and the locking portions 352 of the pressing metal plate 301 engage with the pressing metal plate engagement portions 315. In this case, in the polarization element holding member 304, the bosses 312 are inserted into the boss holes 340 of the packing 302 and the boss holes 353 of the pressing metal plate 301 so that the packing 302 and the pressing metal plate 301 are positioned. In the polarization element holding member 304, screws 390 are inserted into the adjustment holes 357 of the pressing metal plate 301, and screws 390 are screwed into the screw holes 310 to install the reflection-type polarization element 12, the packing 302, and the pressing metal plate 301.

Accordingly, the polarization optical apparatus 300 has dustproof performance of the periphery of the reflection-type polarization element 12, and absorbs a difference in deformation amount caused by a difference in linear expansion coefficient between the reflection-type polarization element 12 and the parts (e.g., the pressing metal plate 301 and the polarization element holding member 304) that hold the reflection-type polarization element 12 due to sliding of the reflection-type polarization element 12. Thus, the polarization optical apparatus 300 is capable of reducing distortion due to deformation of the reflection-type polarization element 12 and enhancing a focus plane on a projected image and a deviation of a pixel position, unlike a fixed reflection-type polarization element in related art.

Further, in the polarization optical apparatus 300, the reflection-type polarization element 12 is not adhered and fixed. Accordingly, reworking becomes easy and it is possible to reduce a manufacturing cost. Further, in the polarization optical apparatus 300, it is possible to realize the holding of the reflection-type polarization element 12 and the sealing of the rim portion of the reflection-type polarization element 12 at a relatively low cost.

The polarization element holding member 304 includes two engagement claws 317 provided in an upper surface and two engagement claws 317 provided in a lower surface, and the engagement claws 317 engage with the engagement portions 330 of the modulation element-side cover 305. The modulation element-side cover 305 includes a window portion 332, and the skirt 306 is fitted to the window portion 332.

The skirt 306 includes a window portion 333 that the reflection-type optical modulation element 14 faces. The skirt 306 is a cylindrical sealing member that seals between the modulation element-side cover 305 and the reflection panel unit 200. The skirt 306 can be greatly deformed by having elasticity and can maintain a sealing structure even when an adjustment amount of a mounting position of the reflection panel unit 200 is relatively great.

The modulation element-side cover 305 is made of aluminum for heat dissipation rather than a low linear expansion coefficient. The modulation element-side cover 305 engages with a surface of the polarization element holding member 304 that the reflection-type optical modulation element 14 faces and separates the surface that the reflection-type optical modulation element 14 faces and a light output surface directed to the color synthesis prism 15 by means of a packing pressing portion 331.

In the polarization element holding member 304, the frame faces, in an angular U-shape, a light output surface directed to the color synthesis prism 15. The light output surface directed to the color synthesis prism 15 forms a frame in a picture frame shape using the angular U-shaped frame and the packing pressing portion 331. The polarization optical apparatus 300 presses the packing 307 against the color synthesis prism 15 by means of the angular U-shaped frame of the polarization element holding member 304 and the packing pressing portion 331.

The polarization element holding member 304 includes prism contact surfaces 320 provided at two end portions and two corners of the angular U-shaped frame facing the color synthesis prism 15. The prism contact surfaces 320 are tip surfaces of boss-shaped protrusions protruding from the packing pressing portion 321. As the prism contact surfaces 320 contact the prism block 110 of the color synthesis prism 15, the polarization optical apparatus 300 is positioned with respect to the color synthesis prism 15 with high accuracy.

The packing 307 is formed of an elastic material (e.g., rubber) and seals between the prism block 110 and the polarization optical apparatus 300. The packing 307 is in a schematically rectangular picture-frame shape and includes notches provided at four corners to avoid interference with the prism contact surfaces 320.

Thus, the polarization optical apparatus 300 reduces influence of heat deformation of the reflection-type polarization element 12 while securing dust-proof spaces from the reflection-type polarization element 12 to the reflection panel unit 200 and from the reflection panel unit 200 to the color synthesis prism 15. Accordingly, the polarization optical apparatus 300 realizes a high-precision image performance (in-plane focus and pixel position) state.

Further, while the embodiment in which the urging portions 356 contact the reflection-type polarization element 12 has been described, the urging portions 356 may contact the packing 302 and urge the reflection-type polarization element 12. That is, the reflection-type polarization element 12 is slid between the sliding surface 314 and the packing 302. In this case, the surface of the packing 302 may be subjected to surface treatment (e.g., lubricant coating) to increase a sliding property.

Further, while the embodiment in which the four urging portions 356 contact the reflection-type polarization element 12 has been described, the number of urging portions 356 may be one, or two or more within a range in which the sliding property of the reflection-type polarization element 12 is not obstructed. For example, the polarization optical apparatus 300 may include one, two, or four urging portions 356.

Additionally, the present technology may also be configured as below.

(1) A polarization optical apparatus including:

a reflection-type polarization element for transmitting a predetermined polarization component light, inputting the light to a reflection-type optical modulation element, and reflecting polarization component light optically modulated by the reflection-type optical modulation element;

a polarization element holding member including a sliding support surface for slidably supporting the reflection-type polarization element in a surface direction, and holding the reflection-type polarization element; and an urging portion for urging the reflection-type polarization element toward the sliding support surface while enabling the reflection-type polarization element to be slid along the sliding support surface.

(2) The polarization optical apparatus according to (1), including:

a reflection-type polarization element sealing member sandwiched between the polarization element holding member and a pressing member including the urging portion to seal a rim portion of the reflection-type polarization element.

(3) The polarization optical apparatus according to (2), wherein the urging portion is supported by a support portion protruding from a window frame portion forming a window portion of the pressing member and faces the window portion.

(4) The polarization optical apparatus according to claim 2, including
an adjustment unit for adjusting an urging force of the urging portion.

(5) The polarization optical apparatus according to any one of (1) to (4), wherein
the sliding support surface supports a rim portion of the reflection-type polarization element.

(6) The polarization optical apparatus according to (5),
wherein the reflection-type polarization element is rectangular, and
wherein the sliding support surface supports four sides of the reflection-type polarization element.

(7) The polarization optical apparatus according to (5) or (6), wherein
the polarization element holding member includes a guide portion for guiding sliding in a surface direction of the reflection-type polarization element.

(8) The polarization optical apparatus according to any one of (1) to (7), wherein
the polarization element holding member includes:
a rectangular output surface for outputting the polarization component light reflected by the reflection-type polarization element toward a color synthesis prism; and
a plurality of color synthesis prism contact surfaces located in corner portions of a frame forming the output surface and contacting the color synthesis prism.

(9) The polarization optical apparatus according to (8),
wherein the polarization element holding member includes a frame forming the output surface, and
wherein the color synthesis prism contact surface protrudes from the frame.

(10) The polarization optical apparatus according to (9), wherein
the frame has an angular U-shape that is opened in a direction that the reflection-type optical modulation element faces.

(11) The polarization optical apparatus according to (10), including:
a cover member including a window portion that the reflection-type optical modulation element faces, the cover member being provided on a surface that the reflection-type optical modulation element of the polarization element holding member faces.

(12) An optical apparatus including:
a plurality of polarization optical apparatuses for outputting polarization component lights optically modulated by reflection-type optical modulation elements; and
a color synthesis prism for receiving, synthesizing and outputting the polarization component lights from the plurality of the polarization optical apparatuses,
wherein the polarization optical apparatus includes
a reflection-type polarization element for transmitting a predetermined polarization component light, inputting the light to a reflection-type optical modulation element, and reflecting polarization component light optically modulated by the reflection-type optical modulation element,
a polarization element holding member including a sliding support surface for slidably supporting the reflection-type polarization element in a surface direction, and holding the reflection-type polarization element, and
an urging portion for urging the reflection-type polarization element toward the sliding support surface while enabling the reflection-type polarization element to be slid along the sliding support surface.

(13) The optical apparatus according to (12), including:
a color synthesis prism sealing member sandwiched between the polarization element holding member and the color synthesis prism to seal between the polarization element holding member and the color synthesis prism; and
a cover member including a window portion that the reflection-type optical modulation element faces in a face of the polarization element holding member that the reflection-type optical modulation element faces, the cover member pressing the color synthesis prism sealing member at one side of the color synthesis prism,
wherein the polarization element holding member includes
a rectangular output surface for outputting the polarization component light reflected by the reflection-type polarization element toward the color synthesis prism,
an angular U-shaped frame forming the output surface and pressing the color synthesis prism sealing member, the angular U-shaped frame being opened in a direction that the reflection-type optical modulation element faces, and
a plurality of color synthesis prism contact surfaces located in corner portions of a frame forming the output surface, protruding from the frame, and contacting the color synthesis prism.

(14) A projection apparatus including including:
a light source;
a separation optical component for separating an output light from the light source according to wavelength bands;
a plurality of reflection-type optical modulation elements for optically modulating and reflecting the incident light separated according to wavelength bands;
an optical apparatus for synthesizing and outputting lights according to the wavelength bands after the optical modulation in the reflection-type optical modulation elements; and
a projection unit for projecting and outputting an output light from the optical apparatus,
wherein the optical apparatus includes
a plurality of polarization optical apparatuses for outputting polarization component lights optically modulated by the reflection-type optical modulation elements and
a color synthesis prism for receiving, synthesizing and outputting the polarization component lights from the plurality of the polarization optical apparatuses, and
wherein the polarization optical apparatus includes
a reflection-type polarization element for transmitting a predetermined polarization component light, inputting the light to the reflection-type optical modulation elements, and reflecting the polarization component lights optically modulated by the reflection-type optical modulation elements,
a polarization element holding member including a sliding support surface for slidably supporting the reflection-type polarization element in a surface direction, and holding the reflection-type polarization element, and
an urging portion for urging the reflection-type polarization element toward the sliding support surface while enabling the reflection-type polarization element to be slid along the sliding support surface.

Further, several changes may be made to the above-described embodiments without departing from the gist of the embodiments.

Further, a number of modifications and alterations may be made to the above-described embodiments by those skilled in the art, and the embodiments are not limited to the exact described configurations and application examples.

The present disclosure contains subject matter related to that disclosed in Japanese Priority Patent Application JP 2011-191191 filed in the Japan Patent Office on Sep. 2, 2011, the entire content of which is hereby incorporated by reference.

What is claimed is:

1. A polarization optical apparatus comprising:
a reflection polarization element for transmitting a predetermined polarization component light, inputting the light to a reflection optical modulation element, and reflecting polarization component light optically modulated by the reflection optical modulation element;
a polarization element holding member including a sliding support surface for slidably supporting the reflection polarization element in a surface direction, and holding the reflection polarization element; and
an urging portion for urging the reflection polarization element toward the sliding support surface while enabling the reflection polarization element to be slid along the sliding support surface.

2. The polarization optical apparatus according to claim 1, comprising:
a reflection polarization element sealing member sandwiched between the polarization element holding member and a pressing member including the urging portion to seal a rim portion of the reflection polarization element.

3. The polarization optical apparatus according to claim 2, wherein
the urging portion is supported by a support portion protruding from a window frame portion forming a window portion of the pressing member and faces the window portion.

4. The polarization optical apparatus according to claim 2, comprising
an adjustment unit for adjusting an urging force of the urging portion.

5. The polarization optical apparatus according to claim 1, wherein
the sliding support surface supports a rim portion of the reflection polarization element.

6. The polarization optical apparatus according to claim 5, wherein the reflection polarization element is rectangular, and
wherein the sliding support surface supports four sides of the reflection polarization element.

7. The polarization optical apparatus according to claim 5, wherein
the polarization element holding member includes a guide portion for guiding sliding in a surface direction of the reflection polarization element.

8. The polarization optical apparatus according to claim 1, wherein
the polarization element holding member includes:
a rectangular output surface for outputting the polarization component light reflected by the reflection polarization element toward a color synthesis prism; and
a plurality of color synthesis prism contact surfaces located in corner portions of a frame forming the output surface and contacting the color synthesis prism.

9. The polarization optical apparatus according to claim 8, wherein the polarization element holding member includes a frame forming the output surface, and
wherein the color synthesis prism contact surface protrudes from the frame.

10. The polarization optical apparatus according to claim 9, wherein
the frame has an angular U-shape that is opened in a direction that the reflection optical modulation element faces.

11. The polarization optical apparatus according to claim 10, comprising:
a cover member including a window portion that the reflection optical modulation element faces, the cover member being provided on a surface that the reflection optical modulation element of the polarization element holding member faces.

12. An optical apparatus comprising:
a plurality of polarization optical apparatuses for outputting polarization component lights optically modulated by reflection optical modulation elements; and
a color synthesis prism for receiving, synthesizing and outputting the polarization component lights from the plurality of the polarization optical apparatuses,
wherein the polarization optical apparatus includes
a reflection polarization element for transmitting a predetermined polarization component light, inputting the light to a reflection optical modulation element, and reflecting polarization component light optically modulated by the reflection optical modulation element,
a polarization element holding member including a sliding support surface for slidably supporting the reflection polarization element in a surface direction, and holding the reflection polarization element, and
an urging portion for urging the reflection polarization element toward the sliding support surface while enabling the reflection polarization element to be slid along the sliding support surface.

13. The optical apparatus according to claim 12, comprising:
a color synthesis prism sealing member sandwiched between the polarization element holding member and the color synthesis prism to seal between the polarization element holding member and the color synthesis prism; and
a cover member including a window portion that the reflection optical modulation element faces in a face of the polarization element holding member that the reflection optical modulation element faces, the cover member pressing the color synthesis prism sealing member at one side of the color synthesis prism,
wherein the polarization element holding member includes
a rectangular output surface for outputting the polarization component light reflected by the reflection polarization element toward the color synthesis prism,
an angular U-shaped frame forming the output surface and pressing the color synthesis prism sealing member, the angular U-shaped frame being opened in a direction that the reflection optical modulation element faces, and
a plurality of color synthesis prism contact surfaces located in corner portions of a frame forming the output surface, protruding from the frame, and contacting the color synthesis prism.

14. A projection apparatus comprising:
a light source;
a separation optical component for separating an output light from the light source according to wavelength bands;
a plurality of reflection optical modulation elements for optically modulating and reflecting the incident light separated according to wavelength bands;
an optical apparatus for synthesizing and outputting lights according to the wavelength bands after the optical modulation in the reflection optical modulation elements; and
a projection unit for projecting and outputting an output light from the optical apparatus, wherein the optical apparatus includes
a plurality of polarization optical apparatuses for outputting polarization component lights optically modulated by the reflection optical modulation elements and
a color synthesis prism for receiving, synthesizing and outputting the polarization component lights from the plurality of the polarization optical apparatuses, and
wherein the polarization optical apparatus includes
a reflection polarization element for transmitting a predetermined polarization component light, inputting the light to the reflection optical modulation elements, and reflecting the polarization component lights optically modulated by the reflection optical modulation elements,
a polarization element holding member including a sliding support surface for slidably supporting the reflection polarization element in a surface direction, and holding the reflection polarization element, and
an urging portion for urging the reflection polarization element toward the sliding support surface while enabling the reflection polarization element to be slid along the sliding support surface.

* * * * *